United States Patent [19]

Biegeleisen

[11] Patent Number: 5,022,399

[45] Date of Patent: Jun. 11, 1991

[54] VENOSCOPE

[76] Inventor: Ken P. Biegeleisen, 91 Hudson Ave., Irvington, N.Y. 10533

[21] Appl. No.: 350,061

[22] Filed: May 10, 1989

[51] Int. Cl.⁵ .............................................. A61B 8/06
[52] U.S. Cl. ............................ 128/662.06; 128/660.03
[58] Field of Search ..................... 128/660.03, 662.06, 128/24 A, 4; 604/262, 264, 266

[56] References Cited

U.S. PATENT DOCUMENTS

| | | | |
|---|---|---|---|
| 4,142,412 | 3/1979 | McLeod et al. | 73/194 A |
| 4,231,373 | 11/1980 | Waxman et al. | 128/660 |
| 4,237,729 | 12/1980 | McLeod et al. | 73/861.25 |
| 4,331,132 | 5/1982 | Mukasa | 128/6 |
| 4,341,120 | 7/1982 | Anderson | 73/618 |
| 4,354,502 | 10/1982 | Colley et al. | 128/663 |
| 4,407,293 | 10/1983 | Suarez, Jr. et al. | 128/660 |
| 4,413,630 | 11/1983 | Anderson et al. | 128/661 |
| 4,424,813 | 1/1984 | Havlice et al. | 128/660 |
| 4,512,762 | 4/1985 | Spears | 604/21 |
| 4,517,985 | 5/1985 | Teslawski et al. | 128/660 |
| 4,524,623 | 6/1985 | Terwilliger | 73/633 |
| 4,538,613 | 9/1985 | Rosenberg | 128/395 |
| 4,576,177 | 3/1986 | Webster, Jr. | 128/660.03 |
| 4,582,067 | 4/1986 | Silverstein et al. | 128/663 |
| 4,587,972 | 5/1986 | Morantle, Jr. | 128/660.03 |
| 4,589,419 | 5/1986 | Laughlin et al. | 128/660.03 |
| 4,615,330 | 10/1986 | Nogasaki et al. | 128/662.06 X |
| 4,641,668 | 2/1987 | Namekawa | 128/663 |
| 4,641,912 | 2/1987 | Goldenberg | 350/96.10 |
| 4,665,925 | 5/1987 | Millar | 128/663 |
| 4,681,103 | 7/1987 | Boner et al. | 128/303 B |
| 4,718,422 | 1/1988 | Rosenberg | 128/632 |
| 4,732,156 | 3/1988 | Makamura | 128/660 |
| 4,733,669 | 3/1988 | Segal | 128/663 |
| 4,763,662 | 8/1988 | Yokoi | 128/660 |
| 4,770,185 | 9/1988 | Silverstein et al. | 128/661.08 |
| 4,771,788 | 9/1988 | Millar | 128/661.09 |
| 4,773,899 | 9/1988 | Spears | 604/20 |
| 4,779,624 | 10/1988 | Yokoi | 128/660.03 X |
| 4,781,681 | 11/1988 | Sharrow et al. | 604/96 |
| 4,784,133 | 11/1988 | Mackin | 128/303.1 |
| 4,794,931 | 1/1989 | Yock | 128/660.03 |
| 4,824,225 | 4/1989 | Nishioka | 350/432 |
| 4,841,977 | 6/1989 | Griffith et al. | 128/660.03 |
| 4,846,155 | 7/1989 | Kimura | 128/6 |
| 4,856,529 | 8/1989 | Segal | 128/662.04 X |
| 4,887,605 | 12/1989 | Angelsen et al. | 128/660.03 |

OTHER PUBLICATIONS

C. R. Appleby, "New Ultrasound Method Offers a Look Inside Blood Vessels," *Healthweek*, Dec. 27, 1988.
J. Ballenot, "Intravascular Sonic Catheter Imaging Shows Big Potential," *Cardio News*, Jan. 1989, pp. 15–21.
Endosonics, "The Cathscanner I ™ System".
Surgiter®, Operator's Manual for Surgiflex ™ Ureteroscopes Models SU-7 and SU9 (1988).
M. Young, "Pleasanton Firm's Unique Ultrasound Catheter Nears Market," *The Alameda Times-Star*, Mar. 28, 1989.

*Primary Examiner*—Francis Jaworski
*Attorney, Agent, or Firm*—Pennie & Edwards

[57] ABSTRACT

A method and apparatus for the non-surgical treatment of venous disorders and varicose veins wherein a flexible catheter is inserted into a varicose vein of a patient to be treated, guiding the catheter to the initial branch of the vein while viewing and monitoring blood flow therein to assure proper position and directing a treatment through the catheter to treat the varicose vein. The catheter of the invention includes first and second passages for directing a fluid and treatment to the distal end of the catheter, first and second fiber bundles to illuminate and view the vein, at least one piezoelectric crystal located on the distal end of the catheter for monitoring areas adjacent thereto and a guide wire for guiding the distal end of the catheter through the veins of the patient.

40 Claims, 4 Drawing Sheets

VENOSCOPE

TECHNICAL FIELD

The invention relates to a modified angioscope having special features which render it ideally suited for the non-surgical treatment of venous disorders and varicose veins in particular. Thus, the inventive device is called a "venous angioscope" or simply, a "venoscope."

BACKGROUND ART

Venous disorders, especially varicose veins, are extremely common, afflicting tens of millions of Americans. The treatment of varicose veins has always been controversial, because no perfect treatment exists.

There is substantial data indicating that the differences between the veins of varicose people and "normal" (i.e., non-varicose) people are not limited to the diseased veins, but bear as well on the apparently normal ones. In other words, whatever forces are responsible for the conversion of a normal vein to a varicose vein are present and acting upon the apparently normal veins adjacent to the varicose veins on the same leg. It is now universally accepted that no existing treatment will prevent veins which are normal now from becoming varicose in the future.

Above and beyond the fact that the varicose predisposition cannot be permanently cured, the recognizably abnormal varicose veins currently present, toward which all therapeutic modalities are directed, are not easily removed. In certain respects, removal of a varicose vein is like removal of a malignant tumor. Any part of the venous network which is contributing to the varicosity, and which is left behind by the surgeon, can and will give rise to a total treatment failure.

The key word here is "network"—the venous system is a continuous network of connected vessels, and in many instances the distinctions drawn between different veins in anatomy texts are arbitrary. For example, the main deep vein of the leg is called the "popliteal" vein below the knee, and the "femoral" vein above the knee. But there's no discontinuity between these veins—they are the same long tube, half of which having one name, and the other half having another name. Similarly, many veins change names at junctions with other similar sized vessels. But there is no reason why a disease afflicting a named vein will stop at a point where the name of the vein changes.

Figure 1:
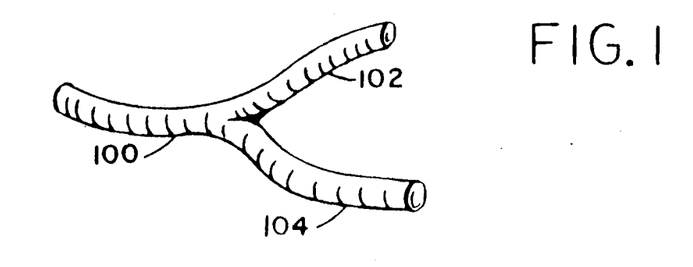
FIGS. 1, 2A, 2B, 2C, 3A, 3B, 3C, 4A, 4B and 5 are illustrations of different veins to show what happens when some of these veins are removed.

In FIG. 1, vein 100 is shown as branching into veins 102 and 104. If vein 100 was a varicose vein, and surgical removal of vein 100 were deemed to be the treatment of choice, then the treatment would work if and only if veins 102 and 104 were normal.

Figure 2A:
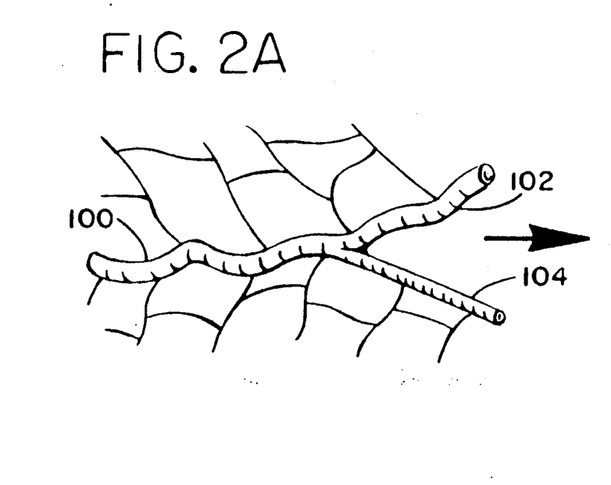
Figure 2B:
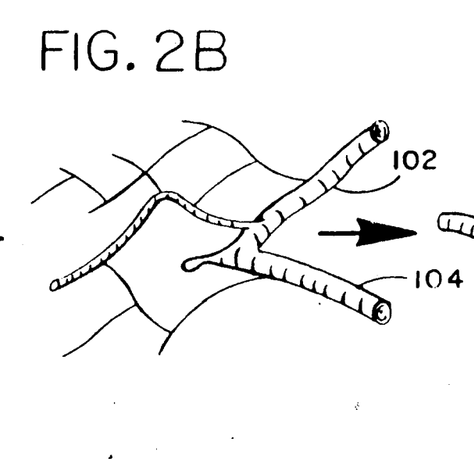
Figure 2C:
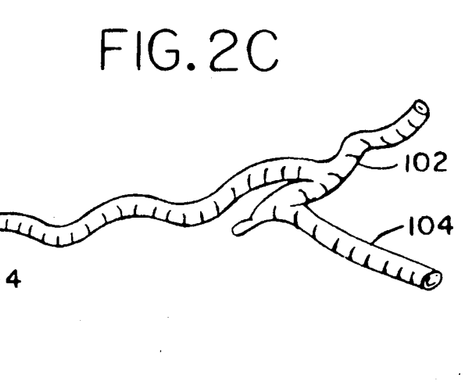

Unfortunately, the real situation is that vein 100 might be a visible, palpable vein on the surface of the leg, and veins 102 and 104 might be buried deep in the calf or thigh muscles, or somewhere in the pelvis. If either of veins 102 or 104 is a contributing factor to the varicose condition of vein 100, then failure to remove 102 and 104 along with 100 at the time of surgery will lead to rapid recurrence of varicosity. Suppose, for example, that vein 102 is abnormal. FIG. 2 illustrates how failure to remove vein 102 will lead to recurrent varicosity.

Note that there are numerous small, seemingly insignificant and unnamed veins in the network of vessels connecting and surrounding 100, 102, and 104. (FIG. 2A) After vein 100 is removed, the pressure formerly exerted on it by vein 102 now bears on the small unnamed vessels of the network. (FIG. 2B) In as short a time as 3-6 months, one or more formerly small vessels in the network will have undergone varicose degeneration, and the patient will return to the surgeon looking as if the operation had never been done. (FIG. 2C)

Figure 3A:
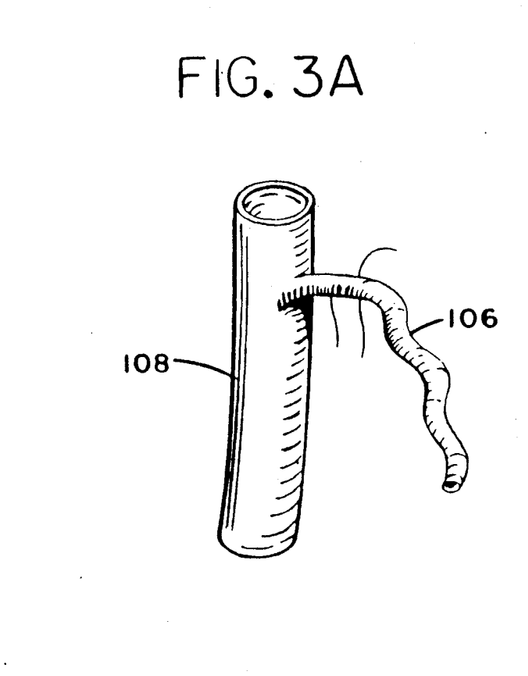
Figure 3B:
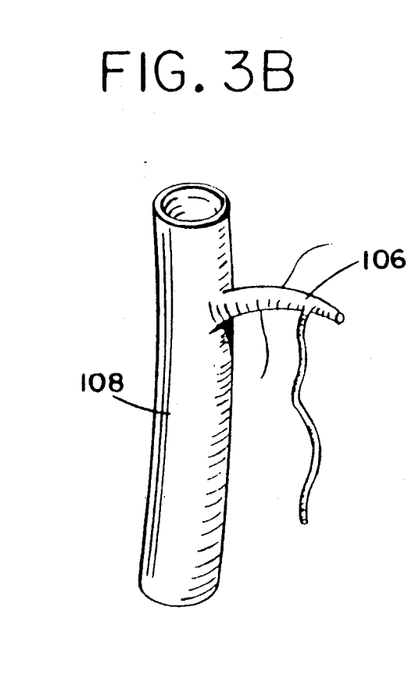
Figure 3C:
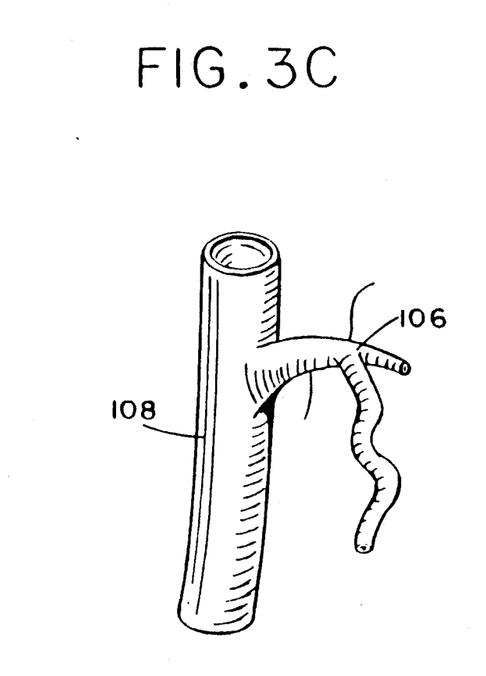

FIG. 3 illustrates a slightly different way in which incomplete surgery can lead to recurrence. The best-known and most frequently treated of all veins subject to varicosity is the greater saphenous vein 106. The segment of the venous system bearing this name begins at the medial (inside) ankle, just in front of the medial malleolus (inside ankle bone), and extends along the inside of the leg all the way to the groin, where it joins the femoral vein 108, at a point called the saphenofemoral junction. There are a few small vessels, referred to as tributaries, entering the saphenous vein 106 just below this junction. The actual number of such tributaries is variable, generally numbering between 3 and 8. (FIG. 3A) If the surgeon cuts the saphenous vein 106 below these tributaries, (FIG. 3B) one or more of them will dilate and the patient returns in 1-12 months with a new varicose vein that looks just like the old one that was removed. (FIG. 3C).

Figure 4A:
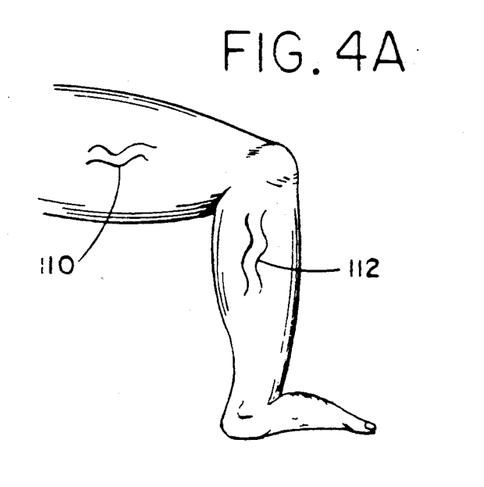
Figure 4B:
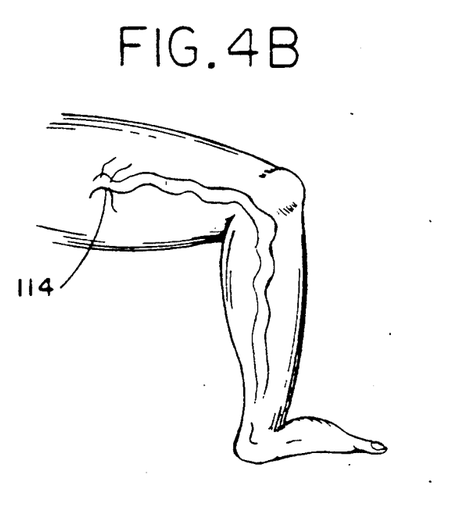

Since 1851, varicose veins have been treated by injection therapy. This treatment is now called "sclerotherapy". The medicines injected are called "sclerosing solutions", or simply "sclerosants". All the early attempts had unacceptably high failure rates, largely because of the lack of attention to the sort of anatomical features outlined above. In the case of the greater saphenous vein, for example, a varicose vein might protrude through the skin at two or three places as shown in FIG. 4A. The vein, however, actually runs all the way up from the ankle to the groin as shown in FIG. 4B.

The old-time injectionist or sclerotherapist would inject a sclerosing treatment solution at each of the blue bumps 110 and 112 (FIG. 4A), totally ignoring the top of the vein where all those tributaries 114 are: (FIG. 4B) For reasons illustrated in FIGS. 2 and 3, this treatment usually failed within a year or two. The sclerotherapist's answer to this problem, in the early days, was to insist on annual check-ups, at which time the recurrent varicosities would be re-treated. There would be no end to the annual checkups.

Figure 5:
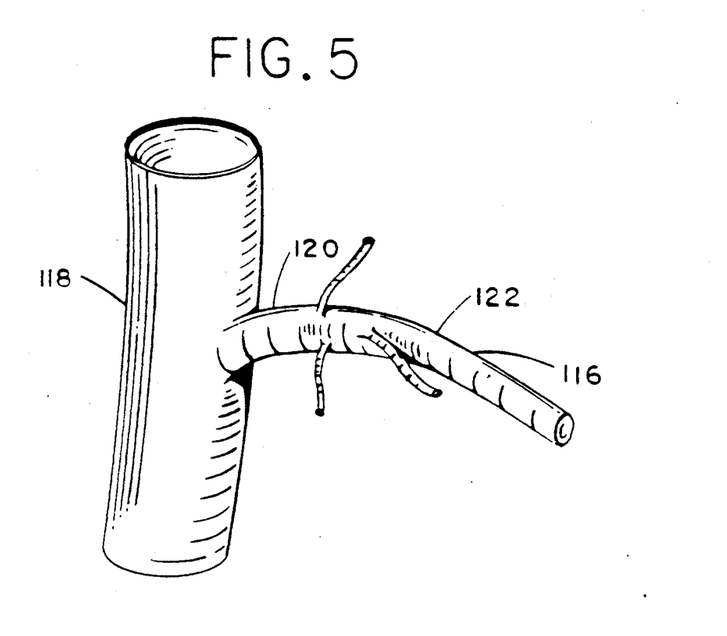

The surgical approach to varicosity is the stripping operation, invented by Charles Mayo at the clinic bearing his name at around 1900. The original stripping operation proved, on long term followup, to have roughly a 50% failure rate. It was 30-40 years before surgeons figured out what was wrong. The main problem was the tributaries. Mayo did not realize the importance of cutting the saphenous vein 116 precisely at its junction with the femoral vein 118, at a point above the highest of the tributaries. FIG. 5 illustrates the proper 120 (operation is successful) and improper 122 (operation fails) locations for this cut.

The major achievement of the post-Mayo vein stripping researchers was the realization of the importance of the absolutely flush saphenofemoral ligation and division, with simultaneous ligation of all the tributaries.

In spite of this increased meticulousness of varicose vein surgery, the existing procedures still fail to bring about even short-term remission from varicosity in 10-20% of cases. Efforts to improve on these figures with a variety of more aggressive and mutilating operations, developed and tested between 1940 and 1960, were uniformly unsuccessful, and today, nearly a century after the invention of the Mayo stripping, it remains in only slightly modified form the treatment of choice for severe saphenous varicosity.

The reasons for the high failure rate with surgery (the failure rate with injection sclerotherapy being even higher) are complex and multifactorial. The known reasons are listed now:

1. The deep veins may be diseased. In the presence of severe deep venous disease, rapid recurrence of surface varicosity cannot be prevented.
2. Varicosity may be associated with multiple small arteriovenous malformations. Surgical interruption of hundreds of tiny arteriovenous communications is generally not feasible.
3. The saphenous vein may be double, triple, or even quadruple. When a duplicate saphenous vein is present, it is usually quite small, and is likely to be missed during surgery. But after the primary saphenous is removed, the duplicate will rapidly enlarge.
4. In spite of the best efforts of the surgeon, a tributary of the saphenous vein might be missed.
5. A varicose vein which appears, at first glance, to start at the groin, may actually start in the pelvis. As explained above, failure to treat the pelvic component inevitably leads to recurrence.
6. A varicose vein which appears to be a result of disease of the short saphenous vein, a vein which extends from the back of the knee (popliteal space) to the ankle, may actually originate deep in the muscles of the calf, or may enter the muscles of the thigh and terminate somewhere far removed from the popliteal space. If these anomalous veins are not taken into account, recurrence is inevitable.

The present invention is designed to overcome the shortcomings of available treatments, especially with respect to the problems listed above. The first two items on the above list cannot be overcome by any forseeable technological advance, but the last four are well known and frequent causes of treatment failure; causes which can be avoided if the treatment takes advantage of the special characteristics of the invention.

SUMMARY OF THE INVENTION

The present invention is a modified angioscope or "venoscope" which is particularly well suited for the non-surgical treatment of venous disorders. The venoscope comprises a flexible catheter having a proximal end and a distal end, means for directing a fluid from a fluid source to the distal end of the catheter, fiberoptic means for viewing areas adjacent the distal end of the catheter, means for guiding the distal end of the catheter through the veins of a patient and means for ultrasonically monitoring areas adjacent to the distal end of the catheter. The directing means, viewing means, guiding means and monitoring means are all located within the body of the catheter.

It should be noted at the outset that the main strength of the venoscope is the incorporation of fiberoptic viewing means and ultrasonic monitoring means into a single instrument. Vascular catheters embodying either one or the other of these means are well known in the prior art and have been exploited mainly for coronary blood flow and peripheral arterial studies. In the venous system, however, it is not sufficient to merely see the inner wall of the vessel, nor is it sufficient to merely measure the velocity of blood flow. In the venous system, the direction of blood flow is of critical importance.

In arteries, blood always flows away from the heart. In veins, however, the direction of blood flow may be either toward or away from the heart. In both the diagnosis and treatment of venous disorders, the determination of the direction of blood flow is essential. Ultrasound provides a means of determining both the velocity and direction of blood flow.

At the same time, the placement of a catheter at the correct anatomical site in the venous system, for diagnosis and treatment, is immensely facilitated by the direct vision afforded by fiberoptics. Because virtually all vascular work performed via catheters has been limited to the arterial system, the importance of combining fiberoptic viewing means and ultrasound monitoring means into a single instrument has not been appreciated by those otherwise skilled in this art. But for applications limited to venous work, a specialty known as Phlebology which is rarely practiced in the United States and which is not comprehensively taught in any U.S. medical school, the need for both fiberoptic and ultrasonic means in a single instrument is fully appreciated.

The ultrasonic monitoring means may be a pulsed wave or continuous wave doppler device. Preferably, the monitoring means is one or more piezoelectric crystals. A single crystal may be split or several individual crystals may be employed. The crystals may be either fixed to provide flow data, or moved to scan an area and create a two-dimensional image. If multiple crystals are used, they may be either internally or externally focused. Internal focusing and beam steering can be accomplished either statically or dynamically.

The venoscope is provided with a fluid directing means to inject treatment solutions into the veins which are preferably channels extending longitudinally through the catheter. Several of these channels, of almost any cross section, may be used depending upon the nature of the venous disorder and the type of treatment required. In the preferred embodiment, there are two such channels. The first channel may be used for injecting a cleansing fluid, such as saline, to flush the blood from the vein while the second may be used for injecting a treatment solution, such as an adhesive or a sclerosant, or for passage of a conducting wire for therapeutic electro-cauterization.

Optical fiber bundles provide means for viewing the areas adjacent to the distal end of the catheter. In a preferred embodiment, there are only two optical fiber bundles. A first optical fiber bundle is attached to any suitable light source and is therefore used to illuminate the distal end of the catheter. The second optical fiber bundle may be connected to an eyepiece at the proximal end of the catheter to facilitate the viewing process. Alternatively, the second bundle may be connected to a video coupler to permit the attachment of a video camera. The image produced by the video camera is then projected onto any suitable video monitor.

The guiding means may be provided by a guide wire or wires capable of changing the direction of the catheter tip so that the operator can safely guide the catheter through the veins of the patient. The guide wires may be passed through additional channels in the catheter or attached in any other convenient way.

An alternate embodiment of the invention relates to a venoscope as described above which further comprises a laser and means to direct a laser beam to ablate an obstruction found in the vein, or to therapeutically cauterize the inner lining of the vein (the intima).

BRIEF DESCRIPTION OF THE DRAWINGS

The nature, advantages and various other additional features of the invention will appear more fully upon consideration of the illustrative embodiments now to be described in detail in connection with the accompanying drawing figures, wherein.

DETAILED DESCRIPTION OF THE PREFERRED EMBODIMENTS

As noted above, the invention will be referred to as a venoscope. In essence, it is a catheter through which we enter the vascular system with our eyes and ears. Thus, both visual and auditory access to the vein and to the position of the catheter therein is provided to assist in the determination of the appropriate location for treatment of the varicosity.

Visual access is provided by two fiberoptic bundles running longitudinally through the length of the catheter. A fiber optic bundle preferably comprising many optical fibers made of high optical grade glass or quartz is used. These two optical fiber bundles are generally located in an adjacent parallel relationship within the body of the catheter. One optical bundle is used with an output source such as a Halogen or Xenon lamp to deliver visible light to illuminate the interior of the vein adjacent to the distal end of the catheter. A second optical bundle can be used either with an eyepiece or with a video camera for viewing the image received from the illuminated region. When used with a video camera, the apparatus is further equipped with a suitable video monitor and a video coupler which connects the optical fiber with the camera.

Auditory access, as well as blood flow velocity and directional monitoring capability, is provided by one or more piezoelectric crystals. These crystals are well known in the prior art devices known as doppler flowmeters and ultrasound imaging devices. More recently, catheters developed for arterial blood flow studies have included one or more piezoelectric crystals, located in the distal tips, which operate in these respective modes. These devices are generally referred to as doppler catheters or ultrasonic imaging catheters.

The crystals used in the present invention are extremely small, ranging in size from only a fraction of a millimeter in diameter, and are connected to the outside world by 2-4 wires depending on the number of crystal used and the functions which they perform. When crystals are excited electrically, they vibrate and generate sound in the ultrasonic range. Returning ultrasonic echoes, conversely, cause the crystal to vibrate and generate electricity. The geometry of the crystal determines its operating frequency. Currently, the range of operating frequencies is 1-20 megahertz (MHz). The higher frequencies provide better resolution but poorer tissue penetration. When the crystals are in invasive catheters, however, tissue penetration is not necessary and the higher frequencies are preferred. Crystals operating at 30 MHz and higher are being developed at the present time and will be highly desirable in the venoscope when they become available.

The ultrasonic monitoring means may be a pulsed wave or continuous wave doppler device. The pivotal technology in this device is the transducer which converts electrical energy to ultrasound, and also converts the returning ultrasound reflections back to electricity. The transducer is preferably one or more piezoelectric crystals. These crystals may operate in the continuous mode, that is, they may be dedicated exclusively to the sending or receiving mode. In the continuous mode, the device requires either multiple crystals, or a single crystal which is split into sending and receiving halves. Alternatively, a single crystal may be employed which operates in a pulsed mode. In this mode, the single crystal sends out pulses of ultrasound in the sending mode and then switches to the receiving mode to listen for returning echos.

In its simplest form, the venoscope has a single piezoelectric crystal located in its distal tip which operates in the pulse (discontinuous) mode. In this mode, the crystal alternately sends and receives ultrasound mode. The portion of the ultrasound reflected by moving blood will be frequency-shifted in proportion to the velocity of blood flow. In a preferred embodiment, multiple crystals are employed to form a continuous mode doppler. In the continuous mode, the device adds information about phase shifts in the reflected beam, relative to the phases of the pulses initially sent out. These phase shifts provide directional information. Thus, in this embodiment of the venoscope, the direct visual data provided by fiberoptics is supplemented by ultrasonic data which reveal the velocity and direction of blood flow. All these data combined provide a setting for therapeutic intervention which is unparalleled in accuracy, safety, and control. Even the direct visualization of the outsides of the vessels which is afforded by extensive surgical exposure cannot provide the degree of control available with the venoscope.

In an alternate embodiment, one or more piezoelectric crystals could be mechanically moved so that they could scan or "interrogate" a larger area. By adding timing data to the information to be processed, specifically, the time necessary for each ultrasound pulse to reach a target and be reflected back to the transducer, a 2-dimensional image of the area adjacent to the catheter tip could be created. This mode of operation is known by those skilled in the art as the "B-mode". At the present time, the preferred method of obtaining a B-mode scan with a single crystal involves rotating and/or translating a single crystal which is affixed to the end of a wire in one channel of the venoscope. One suitable B-mode system is described in U.S. Pat. No. 4,794,931 to Yock which is incorporated herein by reference.

In another embodiment, multiple crystals are mounted in the cathether tip, forming a geometric array. The array may be either externally or internally focused. External focusing requires a lens or mirror, in a manner analogous to the focusing of light rays. Internal focusing, on the other hand, may be either static or dynamic. Static focusing involves shaping the transducer so that unfocused elements (i.e., piezoelectric crystals) will form a focused beam by superposition of unfocused waves. In a preferred embodiment, the ultrasound beam would be dynamically focused and steered. Dynamic focusing, which occurs without any movement of transducer elements, is accomplished by timing the firing of the individual elements in such a way that multiple ultrasound beams reach a defined focal area as if they had been directed there by a physical lens. Such an arrangement is referred to as a phased array of transducer elements.

Some examples of suitable phase array ultrasound imaging systems are those found in catheters produced by Endosonics Corporation of Rancho Cordova, California and Diasonics Incorporated of South San Francisco, Calif. One particularly preferred system is the Endosonics Cathscanner I ™ System.

A recent refinement in image processing, often referred to as color doppler, involves representing blood flow as a color which is superimposed on the gray scale B-mode image of the blood vessel. Such a device, for example, could be programmed so that vessels carrying blood toward the transducer would appear red on the monitoring screen. Similarly, vessels carrying blood away from the transducer would appear blue. The intensity of the color would vary according to the velocity of blood flow. Existing dedicated color doppler devices, none of which embody fiberoptic capability, also give quantitative digital blood flow data. This data supplements the qualitative visual images which appear on the monitoring screens. One preferred embodiment of the venoscope involves the incorporation of an array of piezoelectric crystals providing color doppler to supplement the fiberoptic image.

Current color dopplers, such as those produced by Quantum Medical System of Issaquah, Wash. and that described in U.S. Pat. No. 4,641,668, incorporate suitable transducers which are relatively large. A reasonable representation of blood flow, however, is obtained by the crystal tipped catheter of the current invention when used in combination with its fiberoptic capabilities. It is anticipated that future technology will reduce this transducer to a compatible size.

It should be specifically noted that all the abovementioned modes of ultrasound operation are already in commercial use at the present time. The combination of these ultrasound operations with fiberoptic direct visualization, however, is not known. In all the preferred embodiments of the venoscope, the catheter tip contains piezoelectric elements, which are exceedingly small, and tiny wires connecting them to data processing equipment external to the catheter. Some doppler amplification systems suitable for use in this invention are disclosed in U.S. Pat. Nos. 4,733,669 and 4,771,788 which patents are incorporated herein by reference. The nature of the data processing equipment will depend entirely on the number of piezoelectric crystals in the venoscope, and their operating modes.

The venoscope further comprises at least two injection channels and at least one guide wire channel. Preferably there are two injection channels, one for saline to flush blood from the vein so its interior can be visualized through the optical fibers and one for the injection of a treatment solution, or, alternatively, for passage of an electrical conducting wire for therapeutic cauterization. This treatment solution may be the conventional sclerosants which are used to block the veins. As these veins dissolve, the characteristic blue lines gradually fade away. Instead of these solutions, however, it is possible to inject a vascular adhesive which will displace blood from the vein and seal it from further entry of blood, thus removing the appearance of the blue lines from the patient.

A guide wire is passed through the third channel which may be a central lumen for sliding reception of the guide wire or an elongated open side channel for engaging the guide wire. The guide wire preferably has a diameter of between about 0.02 to 0.03 inches and is capable of changing the direction of the catheter tip so that the operator can safely guide the catheter through the vein or the particular branches which are encountered. Such guide wires are well known in the art and generally comprise a flexible, elongated wire member which is longitudinally inelastic. An example of one such device which may be used in this invention is described in U.S. Pat. No. 4,771,788, the disclosure of which is incorporated herein by reference thereto.

Some prior art fiberoptic devices employ a unique segmented wall structure which facilitates their deformability for the purposes of steering. The deformation is generally accomplished by the operator manipulating a trigger or some other control mechanism, located at the user end of the device. The segmented wall structure increases the outer diameter of a device, but nevertheless, this configuration provides a highly desirable option for venoscopes intended for evaluation and treatment of very large abnormal veins.

Another embodiment of the invention relates to a venoscope further comprising a high energy beam generating device, such as a laser to ablate obstructions found in the vein, or to therapeutically cauterize the venous intima. The laser, which may be of the gas ion, solid state or pulsar type, may be used in unison with the light source along one existing channel or in a separate channel extending through the catheter body dedicated to the laser.

The combination of fiberoptics and doppler in a single device provides advantages particularly well suited for venous work. The catheter described here would have its greatest strength when the treatment solution is a vascular adhesive instead of a sclerosant. The vascular adhesive most widely used has been Bucrylate (2-isobutylcyanoacrylate, formerly distributed by Ethicon). Bucrylate, although not yet F.D.A. approved in the U.S., has proven to be extremely effective in experimental settings, as well as in more ordinary settings in other countries, and appears to have no adverse side-effects. Bucrylate, and other medical grade cyanoacrylates, have been given to countless millions of people over the last few decades without incident.

Bucrylate can be used to permanently seal and shut any abnormal blood vessel. It is potentially a complete replacement for surgical ligation. Its main potential problem is also its main strength, that being its extraordinary ability to close blood vessels. For if injected into the wrong vessel, such as an artery, that one will surely and permanently close down. Therefore, a delivery system for such adhesives through the venoscope described herein would be ideal for delivering Bucrylate, or some other "super sclerosant", to precisely the right area of the right blood vessel. This would prevent accidents due to the injection of sclerosants "blindly" from the surface into the wrong vessel or location.

As an alternative to the cyanoacrylates, a substance known in the medical field as "mussel glue" can be used. This substance is a natural polypeptide that has excellent adhesive properties when wet. As such, it is ideally suited for placement in a vein, which of course is wetted by the blood therein as well as the saline solution which is injected so that the operator can view the vein.

With either adhesive, care must be exercised to assure that the injection passage does not become blocked with cured adhesive. One way to prevent such blockage is to clean the passage after each injection with an appropriate cleaning solution such as water, alcohol, etc. to remove any remaining adhesive from the device. Thereafter, the fluid passages could be disinfected by injecting a solution of glutaraldehyde or idophor as is known in the art for cleaning meterscopes and the like.

Instead of cleaning this fluid passage, the device can be designed to utilize a removable insert made of an engineering thermoplastic, such as a polyacetal or polycarbonate, which could be disposed of after the treatment.

It is also possible to make the fluid passage portion of the device to be removable (or detachable) and thus disposable after one use. Finally, the entire device can be designed to be disposable so that it is only used once, thus avoiding any cleaning or replacement operation after use.

Figure 6:
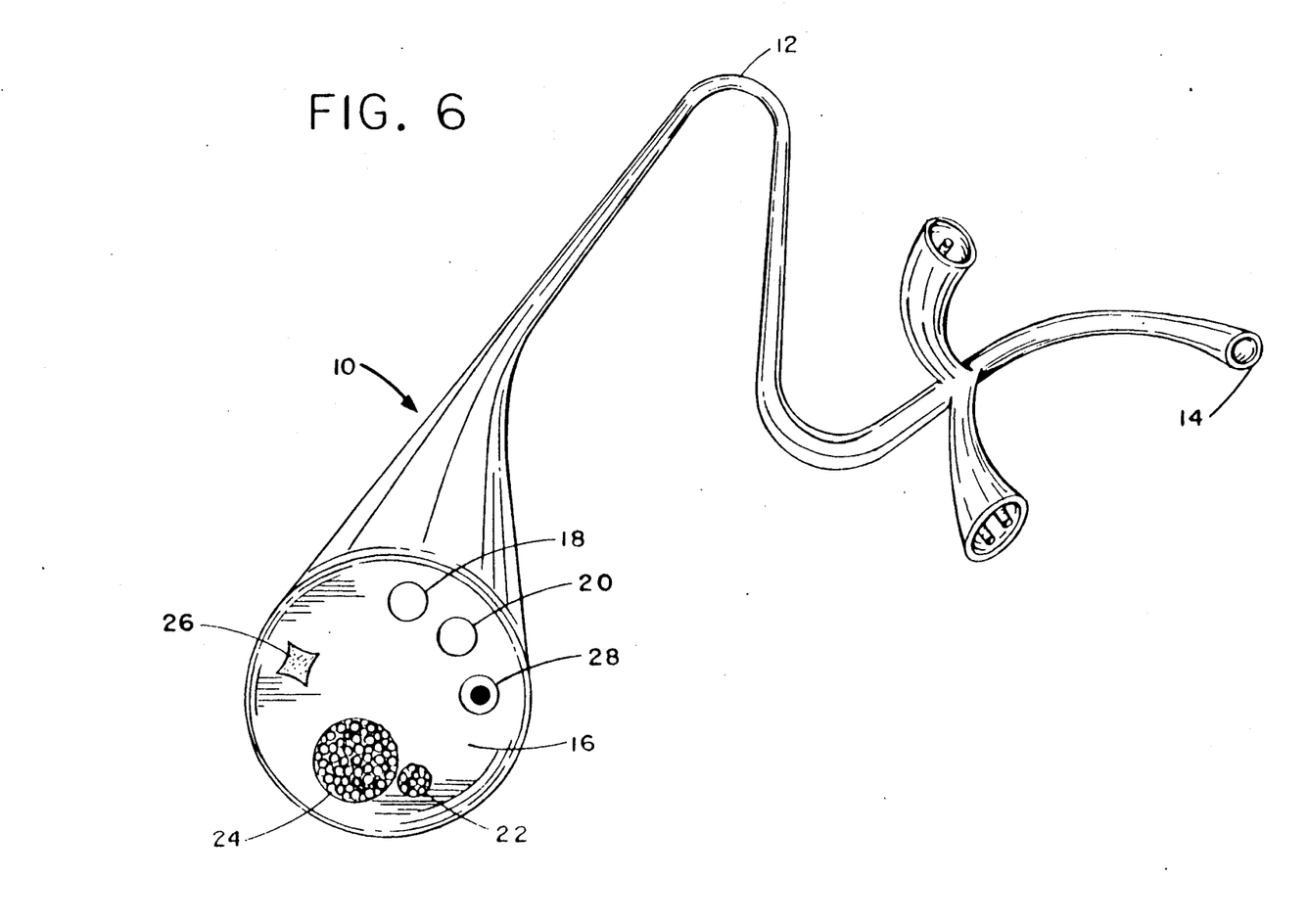
FIG. 6 is a perspective view of a venoscope according to the invention.

Referring now to FIG. 6, venoscope 10 comprises a flexible catheter 12 having a proximal end 14 and a distal end 16. Catheter 12 further comprises first and second passages 18 and 20 for directing first and second fluids to distal end 16 of catheter 12; first and second optical fiber bundles 22 and 24; at least one piezoelectric crystal 26 located at distal end 16 of catheter 12 for monitoring areas adjacent thereto; and guide wire 28 for guiding distal end 16 through the veins of the patient.

Passages 18 and 20 are preferably bores of any suitable cross-section which extend longitudinally through the body of catheter 12. In the preferred embodiment first passage 18 directs saline from a source located near the proximal end 14 to distal end 16 of catheter 12 while second passage 20 directs an adhesive from a source to distal end 16.

Viewing means comprises a first optical fiber bundle 22 for illuminating the region of the vein adjacent to distal end 16 and second optical fiber bundle 24 for viewing the illuminated area. Optical bundles 22 and 24 are placed in a side-by-side arrangement within the body of catheter 12. Preferably, each fiber is made from a high optical grade material such as pure silica and has a diameter of about 0.02 in. or less.

Accordingly, first optical bundle 22 is connected at its proximal end to a light source, such as a Halogen or Xenon lamp (not shown), which directs light towards distal end 16. Second optical fiber bundle 24 receives the image of the illuminated area in the region of distal end 16. This image is transmitted by optical fiber bundle 24 to an eyepiece or via a video coupler to a video monitor for viewing by the physician as venoscope 10 is being positioned within the patient.

Piezoelectric crystal 26 may be any of a number of suitable materials, such as aluminum or silicon oxide, but is preferably a lead-zirconate-titanate material. Crystal 26 is electrically connected to a voltage source by a pair of conductors such that crystal 26 operates as a pulsed doppler mechanism. In one alternate, the crystal may be split into sending and receiving halves with two pairs of conductors emanating therefrom for the continuous mode of doppler operation. As an alternate, the crystal may be located at the end of a wire passing through an additional channel (not shown). The wire would be mechanically rotated by any suitable motor or power source at the user end (not shown), thus causing the crystal to rotate. This rotation enables the crystal to scan the surrounding area, thereby creating a two-dimensional B-mode image of the area. In yet another alternate embodiment, a geometric array of multiple crystals are arranged at distal end 16 of catheter 10, with a corresponding number of pairs of conducting wire. This array could be used, as previously described, to obtain a gray scale B-mode image with or without a color doppler flow pattern superimposed on the gray scale image.

The various wires emanating from the crystal(s) would be connected at proximal end 14 to any suitable processing equipment, which converts the electrical pulses from the crystal(s) to sounds in the audible range, graphic tracings on a continuous chart recorder, or two-dimensional images on a monitor screen.

In the preferred embodiment, guide wire 28 includes an elongated, flexible and longitudinally inelastic support wire made of stainless steel which has an outer diameter of about 0.012 inches. A pair of electrical connector wires are adjoined to the support wire and provide the necessary electrical connections.

EXAMPLES

Turning now to use of venoscope 10 in accordance with the present invention, the following examples are provided to illustrate the preferred embodiments.

EXAMPLE 1

Sclerotherapy of the greater saphenous vein

Catheter 12 is inserted into the saphenous vein at the level of the lower thigh or calf, where it generally bulges through the skin, and is therefore readily accessible. The leg is elevated to drain nearly all blood therefrom. To clear the inside of the vein for visualization, normal saline would be continuously injected through first passage 18. The injection would be accomplished by a continuous infusion pump, of the sort used for the administration of heparin or other IV drugs in the hospital setting. The junction of the saphenous vein with the femoral vein would be identified with absolute certainty by the following: (a) the femoral vein would be red, since no readily attainable infusion of normal saline could clear all the blood from the femoral vein; (b) the length of catheter 12 to be inserted necessary to reach the saphenofemoral junction would be estimated in advance; and (c) the doppler signal generated by crystal 26 in the femoral vein would be heard. This signal differs markedly from the signal of a more superficial vein, and even more so from that of an artery, where the pulsing of the heart is detected.

Having reached the saphenofemoral junction, catheter 12 would be pulled back slightly, and a careful search would be made for orifices to the notorious tributaries, each of which would be entered and injected. Finally, the main trunk of the saphenous would be reentered, and, after tilting the treatment table enough so that the direction of blood flow in the vein was toward the foot (to be determined by visual and doppler cues), a strong sclerosant would be injected into the main trunk via second passage 20. Catheter 12 would be withdrawn, and the leg bandaged according to established principles.

EXAMPLE 2

Sclerotherapy of varicose veins originating deep within calf or thigh muscle, or in the pelvis The basic protocol would be as described above. Catheter 12 would be advanced forward by steps, with an in situ doppler study done at each step. This would continue until either a deep vein was reached (i.e. the popliteal, femoral, or iliac veins), or until an intermediate vein with competent valves were reached (the doppler study would indicate with virtual certainty whether the local valves were competent or not). At such a point, catheter 10 Would be slightly withdrawn, and the incompetent veins injected as described above.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

What is claimed is:

1. A venoscope comprising:
   a flexible catheter having a proximal end, a distal end, and a plurality of passages extending therebetween;
   means for directing a treatment fluid from a fluid source to the distal end of the catheter through at least a first of said passages;
   means for viewing areas adjacent the distal end of the catheter through a second of said passages;
   means extending through another of said passages for guiding the distal end of said catheter through veins of a patient; and
   means for ultrasonically monitoring blood flow in areas adjacent the distal end of the catheter.

2. The venoscope of claim 1 wherein said ultrasonic monitoring means comprises a doppler ultrasound device.

3. The venoscope of claim 2 wherein said doppler ultrasound device comprises one or more piezoelectric crystals capable of operating in various modes to generate blood flow data and an image of the internal vein areas adjacent to said distal end of the catheter.

4. The venoscope of claim 1 wherein said fluid directing means includes at least two first passages in said catheter.

5. The venoscope of claim 4 wherein one of said first passages directs saline from a source to the distal end of the catheter and another of said first passages directs an adhesive or sclerosant.

6. The venoscope of claim 1 wherein said first passage directs saline from a source to said distal end of the catheter and wherein said catheter includes a third passage which includes therein a conductive wire extending from an electrical source to said catheter distal end.

7. The venoscope of claim 1 wherein said viewing means comprises optical fibers.

8. The venoscope of claim 7 wherein said viewing means comprises a first optical fiber bundle disposed in said second passage for illuminating said adjacent interior vein areas and a second optical fiber bundle disposed in a further passage in said catheter for viewing said areas.

9. The venoscope of claim 8 wherein said second optical fiber bundle is connected at said proximal end of said catheter to an eyepiece.

10. The venoscope of claim 8 wherein said second optical fiber bundle is connected at said proximal end of said catheter to a television monitor through a camera.

11. The venoscope of claim 1 further comprising means for removing a portion of interior vein areas adjacent said catheter distal end.

12. The venoscope of claim 11 wherein said removing means extends through a further passage in said catheter and comprises one of means for transmitting a high energy beam or an electrical current therethrough.

13. The venoscope of claim 1 wherein said guiding means comprises a guide wire.

14. A venoscope comprising:
   a flexible catheter having a proximal end, a distal end, and a plurality of passages extending therebetween and further including therein;
   a first and second of said passages for directing first and second fluids, respectively, to the distal end of the catheter;
   a third and fourth of said passages for directing first and second optical fiber bundles, respectively, through the catheter for viewing internal vein areas adjacent the distal end of the catheter;
   at least one piezoelectric crystal located on the distal end of said catheter for monitoring at least one of blood flow and direction in areas adjacent thereto; and
   means for guiding the distal end of said catheter through veins of a patient, said guiding means extending through at least a portion of a fifth of said passages of said catheter.

15. The venoscope of claim 14 wherein a first fluid passage directs saline from a source to the distal end of the catheter and a second passage directs an adhesive or a sclerosant from a source to said catheter distal end.

16. The venoscope of claim 14 wherein a first fluid passage directs saline from a source to the distal end of the catheter and wherein said catheter further comprises a conductive wire extending through a further passage from an electrical source to said catheter distal end.

17. The venoscope of claim 14 wherein said first optical fiber bundle is operatively associated with means for illuminating said internal vein areas and said second optical fiber bundle includes means for viewing said areas.

18. The venoscope of claim 17 wherein said viewing means includes an eyepiece and said second optical fiber is connected at said proximal end of said catheter to said eyepiece.

19. The venoscope of claim 17 wherein said viewing means includes a video camera and a television monitor, and said second optical fiber is connected at said proximal end of said catheter to said television monitor through said video camera.

20. The venoscope of claim 14 wherein said catheter further comprises means to generate a laser beam to remove a portion of said internal vein areas adjacent to said catheter distal end.

21. The venoscope of claim 20 wherein said guiding means comprises a guide wire.

22. A method for treating varicose veins in a patient which comprises:
   inserting into a vein of a patient to be treated, a venoscope comprising a flexible catheter having a proximal end and a distal end, means for directing a treatment from a source to the distal end of the catheter, means for viewing areas adjacent the distal end of the catheter, and means for ultrasonically monitoring areas adjacent the distal end of the catheter, wherein said directing means, viewing means, and monitoring means are located within said catheter;
   guiding the distal end of said venoscope to a branch of said vein while viewing said vein through said venoscope viewing means and monitoring blood flow in said vein by said venoscope monitoring means to assure proper position of the distal end of said venoscope in said vein; and directing a treatment through said venoscope treatment directing means to treat said vein of said patient.

23. A method for delivering a vein treatment solution which comprises inserting into a vein of a patient to be treated, a venoscope comprising a flexible catheter having a proximal end and a distal end, means for directing a fluid from a fluid source to the distal end of the catheter, means for viewing areas adjacent the distal end of the catheter, and means for ultrasonically monitoring areas adjacent the distal end of the catheter, wherein said directing means, viewing means, and monitoring means are located within said catheter, guiding the distal end of said venoscope through the vein to assure proper positioning therein; and introducing said vein treatment solution through said venoscope fluid directing means.

24. The method of claim 22 wherein said treatment is an adhesive.

25. The method of claim 22 wherein said vein is the greater saphenous vein, and said venoscope distal end is directed to the branch from the femoral vein.

26. The method of claim 25 which further comprises sealing tributaries of said greater saphenous vein with an adhesive or sclerosant prior to treating the greater sapherous vein itself.

27. The method of claim 26 wherein the adhesive is an alkyl cyano acrylate, a fatty acid, a hypertonic sclerosant, or a polypeptide.

28. The method of claim 27 wherein the polypeptide adhesive is mussel glue.

29. The method of claim 22 which further comprises treating the vein with a high energy beam to ablate obstructions therein.

30. The method of claim 29 wherein said high energy beam treatment comprises using a laser to treat said varicose vein.

31. The method of claim 22 wherein said treatment comprises using a conductive wire to cauterize said vein.

32. A method for delivering a varicose vein treatment solution which comprises inserting the catheter of claim 1 into a varicose vein of a patient to be treated; guiding the catheter through the vein to assure proper positioning therein; and introducing said solution through said fluid directing means.

33. The method of claim 31 wherein said treatment is an adhesive or a sclerosant.

34. The method of claim 32 wherein the adhesive is an alkyl cyano acrylate, a fatty acid, a hypertonic sclerosant, or a polypeptide.

35. The method of claim 33 wherein the polypeptide adhesive is mussel glue.

36. A method for treating veins in a patient which comprises:
inserting a venoscope comprising a catheter having a proximal end and a distal end into a vein in a patient to be treated;
positioning the distal end of the venoscope at a desired location in said vein by viewing interior portions of said vein and ultrasonically monitoring blood flow therein adjacent the distal tip of said catheter through said venoscope; and
directing a treatment through said venoscope to treat said vein of said patient.

37. The method of claim 36 wherein said treatment is a schlerosing solution, an adhesive, a high energy beam or cauterization.

38. The method of claim 37 wherein said adhesive is an alkyl cyano acrylate, a fatty acid, a hypertonic schlerosant or a polypeptide.

39. The method of claim 35 which further comprises guiding the distal end of the catheter through the catheter to said desired location.

40. The method of claim 35 wherein the treatment of the vein occurs adjacent the distal end of the catheter.

* * * * *

UNITED STATES PATENT AND TRADEMARK OFFICE
CERTIFICATE OF CORRECTION

PATENT NO. : 5,022,399

DATED : June 11, 1991

INVENTOR(S) : Ken P. Beigeleisen

It is certified that error appears in the above-identified patent and that said Letters Patent is hereby corrected as shown below:

Title page, the Attorney, Agent or Firm should read "Pennie & Edmonds".

Signed and Sealed this

Fifth Day of January, 1993

Attest:

DOUGLAS B. COMER

*Attesting Officer*     *Acting Commissioner of Patents and Trademarks*